US011813096B2

(12) United States Patent
Westwood

(10) Patent No.: US 11,813,096 B2
(45) Date of Patent: Nov. 14, 2023

(54) ADJUSTABLE SUPPORT

(71) Applicant: Elekta Limited, Crawley (GB)

(72) Inventor: Anthony Westwood, Crawley (GB)

(73) Assignee: Elekta Limited, Crawley (GB)

( * ) Notice: Subject to any disclaimer, the term of this patent is extended or adjusted under 35 U.S.C. 154(b) by 369 days.

(21) Appl. No.: 17/250,614

(22) PCT Filed: Jul. 29, 2019

(86) PCT No.: PCT/GB2019/052115
§ 371 (c)(1),
(2) Date: Feb. 10, 2021

(87) PCT Pub. No.: WO2020/035654
PCT Pub. Date: Feb. 20, 2020

(65) Prior Publication Data
US 2021/0161491 A1    Jun. 3, 2021

(30) Foreign Application Priority Data

Aug. 15, 2018  (GB) .................................... 1813306

(51) Int. Cl.
*A61B 6/00*        (2006.01)
*A61B 6/03*        (2006.01)
(Continued)

(52) U.S. Cl.
CPC ............ *A61B 6/4447* (2013.01); *A61B 6/035* (2013.01); *A61B 6/037* (2013.01); *A61B 6/4417* (2013.01);
(Continued)

(58) Field of Classification Search
CPC ... A61N 5/1081; A61N 5/1082; A61B 6/4447
See application file for complete search history.

(56) References Cited

U.S. PATENT DOCUMENTS

| 4,741,015 A | * | 4/1988 | Charrier ............... A61B 6/4441 |
| | | | 378/197 |
| 2013/0090514 A1 | * | 4/2013 | Fadler .................. A61N 5/1081 |
| | | | 600/1 |

(Continued)

FOREIGN PATENT DOCUMENTS

| CN | 111887870 A | * | 11/2020 |
| CN | 111938688 A | * | 11/2020 |

(Continued)

OTHER PUBLICATIONS

"International Application Serial No. PCT/GB2019/052115, International Search Report dated Oct. 30, 2019", (dated Oct. 30, 2019), 3 pgs.

(Continued)

*Primary Examiner* — Colin T. Sakamoto
(74) *Attorney, Agent, or Firm* — Schwegman Lundberg & Woessner, P.A.

(57) ABSTRACT

An adjustable support for a gantry (3) for a radiation therapy apparatus or for a medical imaging apparatus, wherein the support comprises: abase (5), a mounting member (1), and an attachment element (7); wherein a lower part of the mounting member (1) engages with the base (5); wherein the attachment element (7) engages with an upper part of the mounting member (1); and wherein the position of the upper part of the mounting member (1), relative to the base (5) is adjustable by the attachment element (7).

25 Claims, 3 Drawing Sheets

(51) Int. Cl.
*A61N 5/10* (2006.01)
*G01R 33/48* (2006.01)
*A61B 5/055* (2006.01)

(52) U.S. Cl.
CPC ............ *A61B 6/482* (2013.01); *A61N 5/1081* (2013.01); *A61N 5/1082* (2013.01); *G01R 33/4808* (2013.01); *A61B 5/055* (2013.01); *A61N 2005/1052* (2013.01); *A61N 2005/1055* (2013.01); *A61N 2005/1061* (2013.01)

(56) References Cited

U.S. PATENT DOCUMENTS

| | | | | |
|---|---|---|---|---|
| 2013/0158382 | A1* | 6/2013 | Chao | A61N 5/1081 600/407 |
| 2015/0320370 | A1* | 11/2015 | Bouvier | A61B 6/4441 378/189 |
| 2016/0022232 | A1* | 1/2016 | Bailey | A61B 6/4447 378/197 |
| 2016/0038109 | A1* | 2/2016 | Fortuna | A61B 6/4458 378/64 |
| 2017/0105691 | A1* | 4/2017 | Shindo | A61B 6/035 |
| 2018/0177473 | A1* | 6/2018 | Gregerson | A61B 6/035 |
| 2018/0220975 | A1* | 8/2018 | Marash | A61B 6/4429 |
| 2019/0090829 | A1* | 3/2019 | Gao | A61B 6/4014 |
| 2020/0054297 | A1* | 2/2020 | Martinez Ferreira | A61B 6/4405 |
| 2020/0330053 | A1* | 10/2020 | Hirose | A61B 6/0487 |

FOREIGN PATENT DOCUMENTS

| | | | |
|---|---|---|---|
| EP | 141135 A * | 5/1985 | ............. A61B 6/037 |
| EP | 3281674 A1 | 2/2018 | |
| EP | 3299064 A1 | 3/2018 | |
| WO | WO-03008986 A2 | 1/2003 | |

OTHER PUBLICATIONS

"International Application Serial No. PCT/GB2019/052115, Written Opinion dated Oct. 30, 2019", (dated Oct. 30, 2019), 5 pgs.

* cited by examiner

ADJUSTABLE SUPPORT

PRIORITY APPLICATIONS

This application is a U.S. National Stage Filing under 35 U.S.C. § 371 from International Application No. PCT/GB2019/052115, filed on Jul. 29, 2019, and published as WO2020/035654 on Feb. 20, 2020, which claims the benefit of priority to United Kingdom Application No. 1813306.6, filed on Aug. 15, 2018; the benefit of priority of each of which is hereby claimed herein, and which applications and publication are hereby incorporated herein by reference in their entireties.

FIELD OF THE INVENTION

The present invention relates to an adjustable support for a gantry, in particular, to an adjustable support for a gantry forming part of a radiation therapy apparatus or medical imaging apparatus.

BACKGROUND OF THE INVENTION

Radiation therapy is a localised treatment designed to treat an identified tissue target (such as a cancerous tumour) and spare the surrounding normal tissue from receiving doses above specified tolerances thereby minimising risk of damage to healthy tissue.

Medical imaging apparatus is used to create visual representations of the interior of a body for diagnosis and clinical intervention.

It is desirable for radiation therapy apparatus to allow more angles that it is possible to irradiate from. This would improve the control of the radiation treatment area and allow more accurately targeted treatment. Further, this would improve the patient experience by moving the radiation therapy apparatus, rather than the patient on the treatment table.

Furthermore, it is desirable for medical imaging apparatus to allow more angles that it is possible to image from. This would improve the control of the imaging area. Further, this would improve the patient experience by moving the medical imaging apparatus, rather than the patient on the treatment table.

The Applicant's prior published international patent application no. WO03/008986 describes a device for use in Image Guided Radiation Therapy (IGRT) which includes the functions of a medical imaging apparatus, particularly, an MRI imaging apparatus in a radiation therapy treatment apparatus and proposes technology for combining these two technologies. The device comprises a large rotating ring gantry onto which a linear accelerator is mounted and arranged to travel around a target positioned at the isocentre of the ring. An MRI sits in the aperture of the ring gantry sharing the isocentre. A body to be treated is introduced into a treatment space at the isocentre by means of a sliding table. The gantry is rotatably mounted and held on a static ring. The static ring is mounted on a base and, together with the base, forms a support assembly for the gantry.

When providing an IGRT apparatus as described above, it is important for the position of the gantry to be adjustable so that the gantry and magnet are aligned. This ensures that the X-ray beam is directed through the gap in the magnet where there is less material to attenuate the beam. Without correct alignment, there is potential for attenuation, scatter and the magnetic field being affected.

Furthermore, the patient support treatment table for IGRT devices is often fixed, rather than being tiltable as for conventional LINAC treatment apparatus. Without a full range of movement of the patient support table there is a potential limitation to the angles it is possible to irradiate from.

In view of the fact that fine positional adjustment is needed once the various components of a large ring gantry are installed in place, it is particularly problematic to provide a support assembly for a radiation therapy apparatus, and/or a medical imaging apparatus, which is not only able to cope with the large forces involved, but which also allows the required fine positional adjustment of the gantry.

The present invention seeks to alleviate these problems.

SUMMARY OF THE INVENTION

According to a first aspect of the present invention, there is provided an adjustable support for a gantry for a radiation therapy apparatus or for a medical imaging apparatus, wherein the support comprises:

a base, a mounting member, and an attachment element;

wherein a lower part of the mounting member engages with the base;

wherein the attachment element engages with an upper part of the mounting member; and wherein the position of the upper part of the mounting member, relative to the base is adjustable by the attachment element.

According to a second aspect of the invention, there is provided a radiation therapy apparatus comprising the adjustable support according to the first aspect of the invention and a gantry, wherein the gantry comprises a radiation source.

According to a third aspect of the invention, there is provided a medical imaging apparatus, comprising the adjustable support according to the first aspect of the invention and a gantry, wherein the gantry comprises a medical imaging apparatus.

According to a fourth aspect of the invention, there is provided an image guided radiation therapy (IGRT) apparatus, comprising the adjustable support according to the first aspect of the invention, wherein the apparatus comprises a radiation source and a medical imaging apparatus.

According to a fifth aspect of the invention, there is provided a method of adjusting the position of an adjustable support for a gantry for a radiation therapy apparatus or for an imaging apparatus according to the first aspect of the invention, comprising moving the attachment member to adjust the position of the upper part of the mounting member, relative to the base.

DETAILED DESCRIPTION

Figure 1:
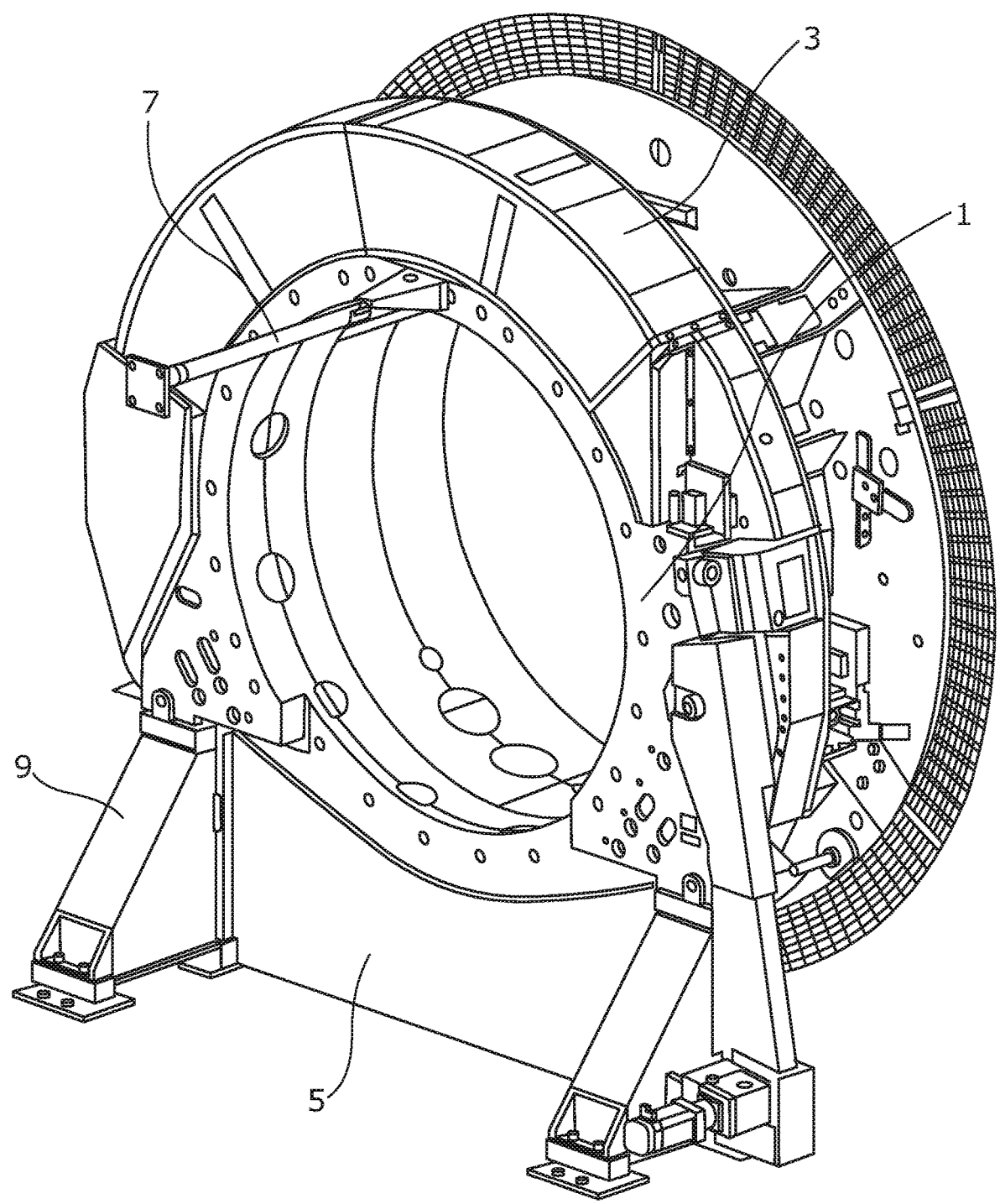
FIG. 1 shows a side view of an adjustable support in accordance with the present invention.

Adjustable Support for a Gantry for a Radiation Therapy Apparatus or for a Medical Imaging Apparatus The present invention relates to an adjustable support for a gantry for a radiation therapy apparatus or for a medical imaging apparatus,
wherein the support comprises:
  a base,
  a mounting member, and
  an attachment element;
wherein a lower part of the mounting member engages with the base;
wherein the attachment element engages with an upper part of the mounting member; and
wherein the position of the upper part of the mounting member, relative to the base is adjustable by the attachment element.

In use, the adjustable support engages with the gantry and allows the position of the support, and thus the gantry to be tilted about the vertical axis. The support is preferably a substantially static ring. The gantry is preferably a rotatable gantry, most preferably a rotatable ring gantry. The rotatable ring gantry preferably has a central opening and the radiation source and/or the medical imaging apparatus, is preferably mounted to the gantry. The gantry is preferably rotatable about the central opening. In use the patient is positioned on a table along the longitudinal direction (x-axis), which is understood to be parallel to the central axis of the gantry and the treatment room floor.

The substantially static ring may be tilted about the vertical axis (z-axis), such as up to 5 degrees from vertical, preferably up to 4 degrees from vertical, more preferably up to 3 degrees from vertical, that is the substantially static ring may be tilted about the vertical axis from 0.1 to 5 degrees from vertical, preferably 0.5 to 4.4 degrees from vertical, more preferably 3.1 to 4.4 degrees from vertical.

The vertical axis is understood to be perpendicular to the treatment room floor and substantially parallel to the upstanding walls of the treatment room.

The "upper part" of the mounting member is understood to refer to the region of the mounting member which is furthest from the treatment room floor. The "lower part" of the mounting member is understood to refer to the region of the mounting member which is closest to the treatment room floor.

The "treatment room floor" has normal meaning in the art and refers to the substantially horizontal surface upon which the adjustable support is directly or indirectly mounted.

In most cases, it is envisaged that the substantially static ring will not move during the radiation therapy treatment or whilst the medical imaging is carried out, but is tilted during installation of the apparatus, and/or prior to commencement of the radiation therapy or medical imaging. In this way, the set up can be completed immediately prior to the radiation treatment or medical imaging commencing.

In other cases, the substantially static ring is tilted about the vertical axis during the radiation therapy treatment or whilst the medical imaging is carried out in order for in situ adjustments to be made.

A particular advantage of the present invention is that it allows fine positional adjustment of the gantry to maximise the degree of freedom to tilt the support and thus the gantry about the vertical axis. This allows the gantry to be rotated about the isocentre to maximise the available treatment or imaging area. In this way, it is possible to pivot the radiation therapy beam, or medical imaging area about the isocentre. This virtual pivot about the isocentre is particularly advantageous as it allows better control of the radiation angles and/or imaging area. Furthermore, the patient experience is improved by making fine adjustments by tilting the adjustable support, rather than having to move the patient.

Preferably, the attachment element connects the upper part of the mounting member to a fixed structure. This gives the adjustable support structural rigidity and helps counteract the forces applied to the support by the weight of the radiation therapy apparatus and/or the medical imaging apparatus, and in particular the forces applied when the radiation therapy apparatus and/or medical imaging apparatus are moved, for example on a rotatable gantry.

Preferably the fixed structure is a wall, ceiling or frame. These fixed structures are suitable for providing structural support to the adjustable support.

Preferably the fixed structure is a wall or a ceiling. These fixed structures may provide a high level of structural support as they are part of the room design.

Preferably the fixed structure is a wall. A wall is able to be connected via an attachment element which is arranged in a substantially longitudinal direction (parallel to the x-axis) which maximises the structural support the wall can provide to the adjustable support as the push-pull force is directed perpendicular to the adjustable support and allows the adjustable support to be tilted with minimal force.

Preferably the wall is substantially vertical which maximises the structural support the wall can provide to the adjustable support.

Preferably the attachment element is arranged in a substantially longitudinal direction. This maximises the structural support that is provide to the adjustable support as the push-pull force is directed perpendicular to the adjustable support and allows the adjustable support to be tilted with minimal force.

Alternatively, the attachment element may not be arranged in a substantially longitudinal direction. This may be advantageous when room constraints mean that it is preferable for the attachment element to be at a different angle. The advantage of having the attachment means in a substantially longitudinal direction and the advantage of a different angle need to be balanced for each installation.

The attachment element is preferably a linear actuator. This has the advantage of the adjustment of the position of the support being easily controlled by the linear motion. Preferably the linear actuator is arranged substantially parallel to the longitudinal axis and provides linear motion along this direction. This means that the force is applied in the most efficient manner to the adjustable support and allows the fine control of the tilting of the adjustable support.

Preferably the attachment element is a mechanical actuator, linear motor actuator, electro-mechanical actuator, hydraulic actuator or moving coil actuator. This means that the force is applied in the most efficient manner to the adjustable support and allows the tilting of the adjustable support to be controlled.

Preferably the upper part of the mounting member is pivotably engaged with the attachment element. This can allow the adjustable support to be tilted efficiently.

Preferably the position of the lower part of the mounting member relative to the treatment room floor is adjustable. This increases the control of the tilting mechanism, as the position of both the upper part and the lower part of the mounting member can be adjusted, which allows the radiation therapy beam, or medical imaging beam to pass through the isocentre for all gantry angles. This allows particularly fine control of the radiation treatment beam or medical imaging apparatus.

Preferably the position of the lower part of the mounting member relative to the base is adjustable. Preferably the base and the lower part of the mounting member are joined together by a linear slide. A linear slide allows motion in one direction and restricts motion in other directions. Preferably the linear slide allows motion in the longitudinal direction (x-axis) which allows the adjustable support to be tilted about the vertical axis (z-axis). An advantage of a linear slide is that it allows fine control of the movement of the adjustable support in the longitudinal direction. Preferably the base is fixed to the treatment room floor which has an advantage of providing structural rigidity, while allowing the adjustable support to be tilted. Preferably the lower part of the mounting member is pivotably engaged with the linear slide. This can allow the adjustable support to be tilted efficiently.

The base and the lower part of the mounting member may be joined together by one or more flexible plates. These flexible plates can allow the lower part of the mounting member to be tilted about the base in a controlled manner. Preferably the one or more flexible plates are positioned in a substantially vertical orientation. This allows fine control of the movement of the lower part of the mounting member relative to the base and allows the lower part of the mounting member to pivot relative to the base.

Alternatively, the base may contact the treatment room floor via a movement mechanism. Preferably the movement mechanism is a track attached to the treatment room floor and the track is arranged substantially along the longitudinal direction, whereby the base engages with the track and is movable along the track. A track helps to ensure the movement of the base relative to the treatment room floor is in a substantially longitudinal direction.

Alternatively, the movement mechanism may be wheels or bearings. Such an arrangement allows for easier installation as the base does not need to fit into a preinstalled track.

Preferably the base comprises two frame feet. This helps the stability of the adjustable support by spreading the weight across two main contact points on the treatment room floor. Preferably the frame feet are spaced substantially equidistant from the centre of the adjustable support. In this way they can effectively support the weight of the adjustable support.

Preferably the position of each frame foot relative to the treatment room floor or to the lower part of the mounting member is simultaneously adjusted. This means that adjustable support is only tilted about the vertical axis by movement in a longitudinal direction. This improves the structural rigidity of the adjustable support.

Alternatively, the position of each frame foot is independently adjustable relative to the treatment room floor or the lower part of the mounting member. This allows for greater freedom in moving the adjustable support.

Preferably the medical imaging apparatus comprises a magnetic resonance imaging (MRI) apparatus, a computed tomography (CT) apparatus, a positron emission tomography (PET) apparatus or a dual energy X-ray absorptiometry (DEXA) apparatus, preferably an MRI apparatus.

A Radiation Therapy Apparatus

The present invention relates to a radiation therapy apparatus comprising the adjustable support as described herein and a gantry, wherein the gantry comprises a radiation source.

Preferably the gantry is a rotatable gantry, more preferably a rotatable ring gantry, which allows the radiation source to be moved to the desired position for radiation therapy.

A Medical Imaging Apparatus

The present invention relates to a medical imaging apparatus, comprising the adjustable support as described herein and a gantry, wherein the gantry comprises a medical imaging apparatus.

Preferably the gantry is a rotatable gantry, more preferably a rotatable ring gantry, which allows the medical imaging apparatus to be moved to the desired position for imaging.

Preferably the medical imaging apparatus comprises a magnetic resonance imaging (MRI) apparatus, a computed tomography (CT) apparatus, a positron emission tomography (PET) apparatus or a dual energy X-ray absorptiometry (DEXA) apparatus, preferably an MRI apparatus.

An Image Guided Radiation Therapy (IGRT) Apparatus

The present invention relates to an image guided radiation therapy (IGRT) apparatus comprising the adjustable support as described herein, wherein the apparatus comprises a radiation source and a medical imaging apparatus.

Preferably the gantry is a rotatable gantry, more preferably a rotatable ring gantry, and comprises the radiation source. Preferably the rotatable gantry does not comprise the medical imaging apparatus. This allows the medical imaging apparatus to be held at a known position, while varying the position of the radiation source.

Alternatively, the rotatable gantry, more preferably a rotatable ring gantry, may comprise the radiation source and the medical imaging apparatus to control the position of both either simultaneously, or independently.

The present invention allows the operator to ensure that the X-ray beam is directed through the gap in the magnet of, for example an MRI apparatus, where there is less material to attenuate the beam.

A Method of Adjusting the Position of an Adjustable Support for a Gantry

The present invention relates to a method of adjusting the position of an adjustable support for a gantry for a radiation therapy apparatus or for an imaging apparatus as described herein, comprising moving the attachment member to adjust the position of the upper part of the mounting member, relative to the base. This allows control of the position of the support, and thus the radiation therapy apparatus and/or medical imaging apparatus.

Preferably the method further comprises moving the lower part of the mounting member relative to the treatment room floor. The base may be fixed to the treatment room floor and the lower part of the mounting member may be moved relative to the base. Alternatively, the mounting member may be fixed to the base and the mounting member and the base may be moved relative to the treatment room floor. This allows greater control of the position of the adjustable support and thus the radiation therapy apparatus and/or medical imaging apparatus.

DETAILED DESCRIPTION OF THE DRAWINGS

The present invention will now be described with reference to the figures. It will be appreciated that the figures do not necessarily limit the scope of the claims.

Referring to FIG. 1, the present invention comprises a mounting member in the form of a static ring 1 for rotatably supporting a dynamic gantry 3. The gantry 3 is rotatably mounted and held on the static ring 1. In the embodiment of FIG. 1, the apparatus is an image guided radiation therapy apparatus (IGRT) and an MRI device (not shown) is mounted within the aperture of the static ring. However, it is understood that in alternative embodiments of the present invention the apparatus is a LINAC radiation therapy apparatus, without an imaging apparatus, or an imaging apparatus without a LINAC radiation therapy apparatus. A body (not shown) to be treated is introduced into a treatment space at the isocentre by means of a sliding table (not shown). The static ring 1 is mounted on a base 5 and supported by an attachment element 7, which together form a support assembly for the gantry 3. The base 5 is mounted on the treatment room floor.

Figure 2:
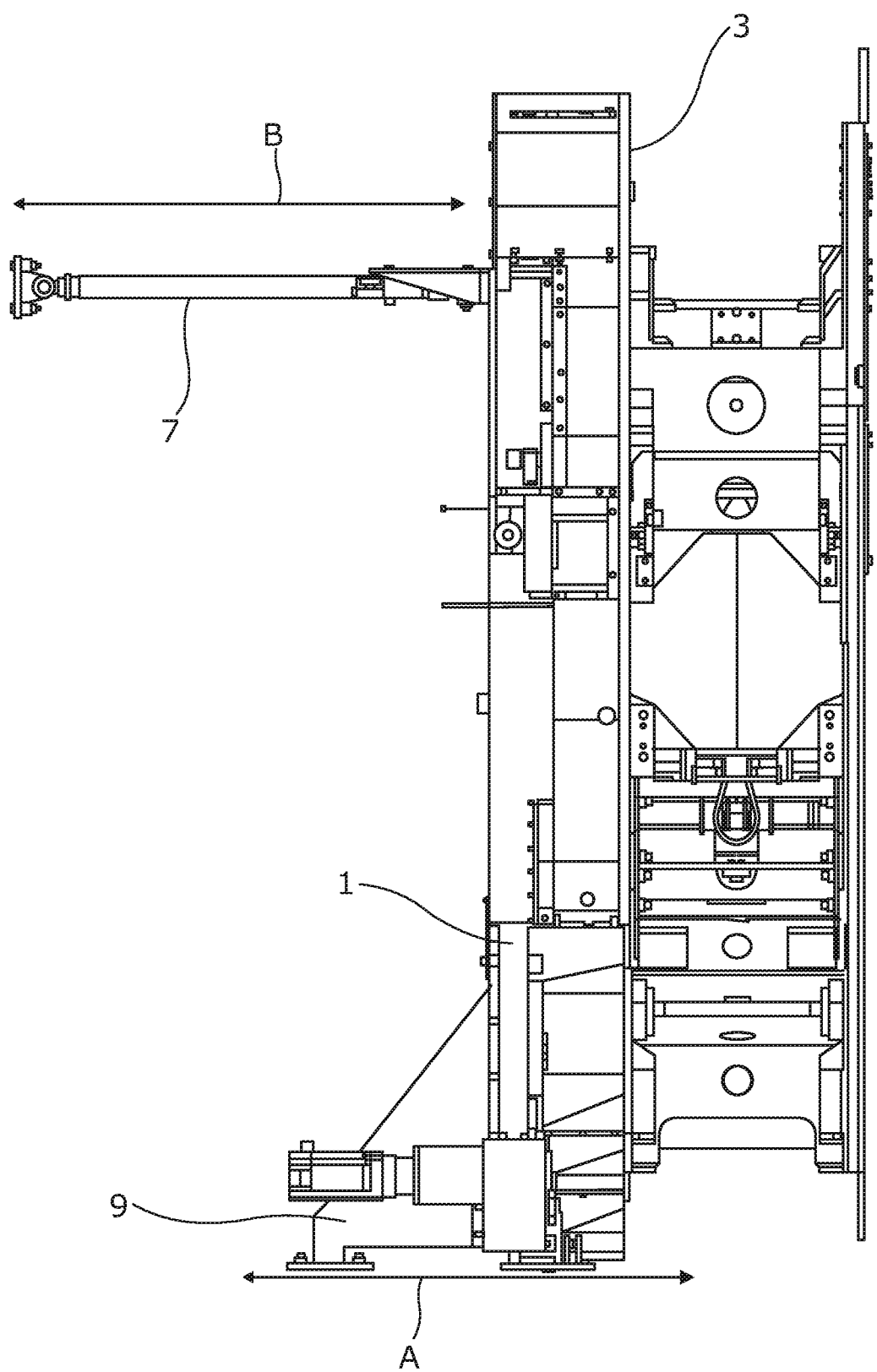
FIG. 2 shows a cross-sectional view of an adjustable support in accordance with the present invention.

As shown in FIG. 1, the static ring is mounted on a base 5, which is supported by frame feet 9. As shown in FIG. 2, the frame feet 9 are mounted on a linear slide, which allows movement of the base in forward and rearward direction along the x-axis as indicated by arrow A in FIG. 1. That is, the frame feet 9 are moveable forwards and backwards in a direction substantially parallel to the longitudinal axis of the treatment table. It will be appreciated that other means of moving the adjustable support fall within the scope of the present invention, such as a movement mechanism comprising a track attached to the treatment room floor which is arranged substantially along the longitudinal direction, whereby the base engages with the track or is moveable along the track. Alternatively, the movement mechanism may be wheels or bearings.

An attachment element 7, in the form of an arm, is provided at the top of the static ring 1 for securing the substantially upright position of the static ring 1 relative to a fixed structure, such as a wall, ceiling or frame, preferably a wall (not shown) of the treatment room. The attachment element 7 is a connection tube of approximately 1.5 m length, such as 0.5 m to 3 m length, preferably 1 to 2.5 m length, preferably 1 m to 2 m length. The connection tube having a first interface with the wall and a second interface with the static ring 1. The attachment element 7 connect the upper part of the static ring 1, for example to the concrete wall of the treatment room and is encapsulated by the RF cage. The "upper part" of the static ring 3 is understood to refer to the region of the static ring 1 which is furthest from the treatment room floor. As shown in FIG. 2, the attachment element 7 is adjustable by means of a linear actuator that moves the top of the static ring towards and way from the wall to which the attachment element is secured in the direction indicated by arrow B (along the x-axis).

By adjusting the position of the upper part of the static ring 1, and optionally the lower part of the static ring 1, a theoretical pivot at the isocentre can be retained without a physical isocentre being present. This ensures that the treatment beam can pass through the treatment isocentre for all gantry angles.

Figure 3:
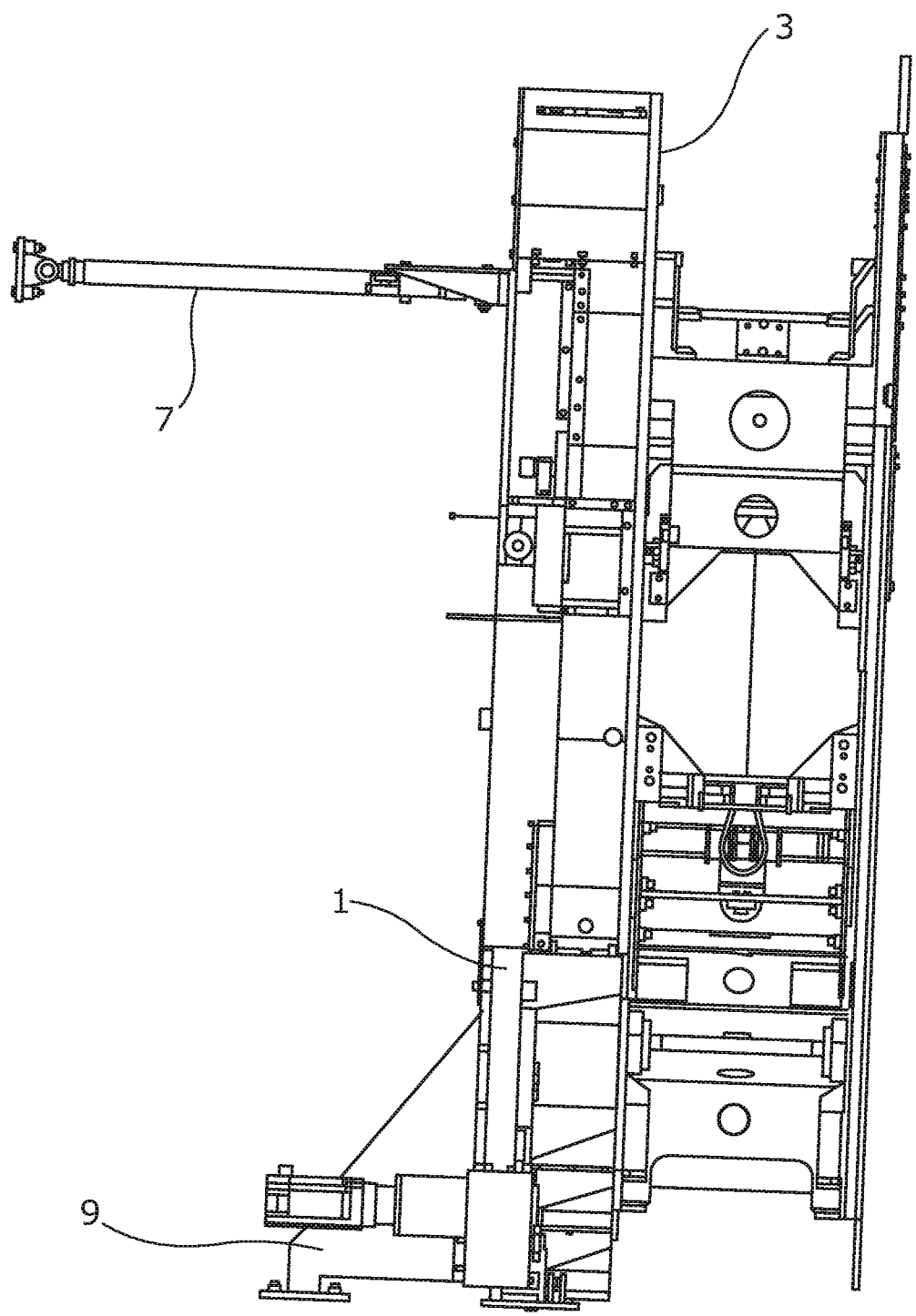
FIG. 3 shows a cross-sectional view of a tilted adjustable support in accordance with the present invention.

FIG. 3 shows the adjustable support in a tilted position. This has been achieved by linear motion of the attachment member 7 along the longitudinal direction B tilting the upper part of the static ring 3 relative to the frame feet 9. Further, the position of the lower part of the static ring 3 relative to the treatment room floor may also have been tilted relative to the treatment room floor by the motion of the linear slide on the frame feet 9 along the longitudinal A direction.

Within this specification embodiments have been described in a way which enables a clear and concise specification to be written, but it is intended and will be appreciated that embodiments may be variously combined or separated without parting from the invention. For example, it will be appreciated that all preferred features described herein are applicable to all aspects of the invention described herein and vice versa.

It will be appreciated that reference to "one or more" includes reference to "a plurality".

Unless specified elsewhere in the specification, substantially means a deviation of ±10%, preferably ±5%, more preferably ±2%, more preferably ±0.1%, most preferably, no deviation.

Further embodiments and simple design variations of the embodiments disclosed herein will no doubt occur to the skilled addressee without departing from the true scope of the claims of the invention as defined in the appended claims.

The invention claimed is:

1. An adjustable support for a gantry for a radiation therapy apparatus or for a medical imaging apparatus, comprising:
 a base;
 a mounting member; and
 an arm arranged in a substantially longitudinal direction parallel to a treatment room floor;
 wherein a lower part of the mounting member engages with the base, wherein the arm engages with an upper part of the mounting member, and wherein a position of an upper part of the mounting member relative to the base is adjustable by the arm.

2. The adjustable support according to claim 1, wherein the mounting member comprises a substantially static ring.

3. The adjustable support according to claim 1, wherein the gantry is a rotatable gantry.

4. The adjustable support according to claim 3, wherein the gantry is a rotatable ring gantry.

5. The adjustable support according to claim 1, wherein the arm connects the upper part of the mounting member to a fixed structure.

6. The adjustable support according to claim 5, wherein the fixed structure is at least one of: a wall, a ceiling, or a frame.

7. The adjustable support according to claim 1, wherein the arm is a linear actuator.

8. The adjustable support according to claim 1, wherein the arm comprises at least one of: a mechanical actuator, a linear motor actuator, an electro-mechanical actuator, a hydraulic actuator or a moving coil actuator.

9. The adjustable support according to claim 1, wherein the base is mounted in a treatment room, and wherein a position of the lower part of the mounting member relative to the treatment room floor is adjustable.

10. The adjustable support according to claim 1, wherein a position of the lower part of the mounting member relative to the base is adjustable.

11. The adjustable support according to claim 1, wherein the base and the lower part of the mounting member are joined together by a linear slide.

12. The adjustable support according to claim 1, wherein the base is fixed to the treatment room floor.

13. The adjustable support according to claim 1, wherein the base contacts the treatment room floor via a movement mechanism.

14. The adjustable support according to claim 1, wherein the base contacts the treatment room floor via a movement mechanism, wherein the movement mechanism comprises a track attached to the treatment room floor, wherein the track is arranged substantially along the longitudinal direction, and wherein the base engages with the track and is moveable along the track.

15. The adjustable support according to claim 1, wherein the base contacts the treatment room floor via a movement mechanism, and wherein the movement mechanism is a wheel or a bearing.

16. The adjustable support according to claim 1, wherein the base comprises at least two frame feet.

17. The adjustable support according to claim 1 wherein the base comprises at least two frame feet and wherein a position of each frame foot relative to the treatment room floor or to the lower part of the mounting member is independently adjustable.

18. The adjustable support according to claim 1, wherein the base comprises at least two frame feet and wherein a position of each frame foot relative to the treatment room floor or to the lower part of the mounting member is simultaneously adjusted.

19. The adjustable support according to claim 1, wherein the adjustable support is included in the radiation therapy apparatus, wherein the radiation therapy apparatus includes and a gantry, and wherein the gantry comprises a radiation source.

20. The adjustable support according to claim 1, wherein the adjustable support is included in the medical imaging apparatus, wherein the medical imaging apparatus includes the gantry, and wherein the gantry comprises a medical imaging apparatus.

21. The adjustable support according to claim 20, wherein the medical imaging apparatus comprises at least one of: a magnetic resonance imaging (MRI) apparatus, a computed tomography (CT) apparatus, a positron emission tomography (PET) apparatus, or a dual energy X-ray absorptiometry (DEXA) apparatus.

22. An image guided radiation therapy (IGRT) apparatus, comprising an adjustable support, the adjustable support comprising:
a base;
a mounting member; and
an arm arranged in a substantially longitudinal direction parallel to a treatment room floor;
wherein a lower part of the mounting member engages with the base, wherein the arm engages with an upper part of the mounting member, and wherein a position of the upper part of the mounting member relative to the base is adjustable by the arm.

23. The image guided radiation therapy (IGRT) apparatus according to claim 22, wherein the IRGT apparatus comprises a radiation source and a medical imaging apparatus, and wherein the medical imaging apparatus comprises at least one of: a magnetic resonance imaging (MRI) apparatus, a computed tomography (CT) apparatus, a positron emission tomography (PET) apparatus or a dual energy X-ray absorptiometry (DEXA) apparatus.

24. A method of adjusting a position of an adjustable support for a gantry for a radiation therapy apparatus or for an imaging apparatus, the adjustable support comprising:
a base;
a mounting member; and
an arm arranged in a substantially longitudinal direction parallel to a treatment room floor;
wherein a lower part of the mounting member engages with the base, wherein the arm engages with an upper part of the mounting member, and wherein a position of the upper part of the mounting member relative to the base is adjustable by the arm;
the method comprising:
moving the arm to adjust the position of the upper part of the mounting member relative to the base.

25. The method according to claim 24, further comprising:
moving the lower part of the mounting member relative to the treatment room floor.

* * * * *

UNITED STATES PATENT AND TRADEMARK OFFICE
CERTIFICATE OF CORRECTION

PATENT NO. : 11,813,096 B2
APPLICATION NO. : 17/250614
DATED : November 14, 2023
INVENTOR(S) : Anthony Westwood Page 1 of 1

It is certified that error appears in the above-identified patent and that said Letters Patent is hereby corrected as shown below:

On the Title Page

Item (57) in "Abstract", in Column 2, Line 3, delete "abase" and insert --a base-- therefor Signed and Sealed this
Fourth Day of February, 2025

Coke Morgan Stewart
*Acting Director of the United States Patent and Trademark Office*